(12) United States Patent
Miyamoto (10) Patent No.: US 8,416,239 B2
(45) Date of Patent: Apr. 9, 2013

(54) INTERMEDIATE IMAGE GENERATION METHOD, APPARATUS, AND PROGRAM

(75) Inventor: Masaki Miyamoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/736,378

(22) PCT Filed: Mar. 31, 2009

(86) PCT No.: PCT/JP2009/001495
§ 371 (c)(1),
(2), (4) Date: Dec. 2, 2010

(87) PCT Pub. No.: WO2009/122725
PCT Pub. Date: Oct. 8, 2009

(65) Prior Publication Data
US 2011/0074781 A1    Mar. 31, 2011

(30) Foreign Application Priority Data
Apr. 3, 2008   (JP) ................................ 2008-097523

(51) Int. Cl.
*G06T 15/00*    (2011.01)

(52) U.S. Cl.
USPC ............ 345/424; 345/591; 382/151; 715/794

(58) Field of Classification Search .................. None
See application file for complete search history.

(56) References Cited

U.S. PATENT DOCUMENTS

| | | | |
|---|---|---|---|
| 6,690,371 B1 * | 2/2004 | Okerlund et al. | 345/424 |
| 6,940,507 B2 * | 9/2005 | Repin et al. | 345/424 |
| 7,190,836 B2 * | 3/2007 | Krishnan et al. | 382/232 |
| 7,623,697 B1 * | 11/2009 | Hughes et al. | 382/133 |
| 7,990,378 B2 * | 8/2011 | Rabben et al. | 345/424 |
| 8,073,285 B2 * | 12/2011 | Curtis | 382/274 |
| 2009/0002366 A1 * | 1/2009 | Kanitsar et al. | 345/419 |
| 2009/0027418 A1 * | 1/2009 | Maru et al. | 345/629 |

FOREIGN PATENT DOCUMENTS

| | | |
|---|---|---|
| JP | 2000-090283 | 3/2000 |
| JP | 2001-084409 | 3/2001 |
| JP | 2005-202791 | 7/2005 |
| WO | WO 2006/048802 | 5/2006 |

* cited by examiner

*Primary Examiner* — Daniel Hajnik
*Assistant Examiner* — Andrew G Yang
(74) *Attorney, Agent, or Firm* — Jean C. Edwards, Esq.; Edwards Neils PLLC

(57) ABSTRACT

When generating an intermediate image which is an image in the middle of changing from one to the other of two pseudo three-dimensional images generated by ray casting a three-dimensional image from an arbitrary viewpoint under two different opacity level setting conditions, determining an opacity level setting condition by determining an opacity level to be allocated according to each pixel value such that a variation in the opacity level for a change in a changing phase of the intermediate image become smaller as the changing phase approaches closer to a pseudo three-dimensional image generated under either one of the two different opacity level setting conditions in which a smaller value is allocated as the opacity level to be allocated according to each pixel value, and generating an intermediate image by ray casting the three-dimensional image from an arbitrary viewpoint under the determined opacity level setting condition.

9 Claims, 6 Drawing Sheets

FIG.8

INTERMEDIATE IMAGE GENERATION METHOD, APPARATUS, AND PROGRAM

CROSS-REFERENCE TO RELATED APPLICATIONS

The present invention is a 35 USC 371 national stage entry of PCT/JP2009/001495, filed Mar. 31, 2009, which claims priority from Japanese Patent Application No. 2008-097523, filed Apr. 3, 2008, the contents of all of which are herein incorporated by reference in their entirety.

BACKGROUND OF THE INVENTION

1. Technical Field

The present invention relates to an intermediate image generation method, apparatus, and program for generating an intermediate image which is an image in the middle of changing from one to the other of two pseudo three-dimensional images generated by ray casting a three-dimensional image under two different opacity level setting conditions.

2. Description of the Related Art

In order to facilitate understanding of a three-dimensional structure of a subject, image processing for generating and displaying a pseudo three-dimensional image which is three-dimensional image data of a subject, constituted by multiple two dimensional images obtained by a CT system, an MRI system, an ultrasonic diagnostic system, or the like, is stereoscopically visualized on a two-dimensional plane using computer graphics technologies.

As for the method of generating such pseudo three-dimensional images, a volume rendering method is known. This is a method for generating a translucent projection image by sampling, based on an opacity level and a luminance value set to each pixel (voxel) constituting a three-dimensional image, these values at each search point along each visual line and adding up the products of these values to obtain a pixel value of each pixel to be projected.

Figure 1:
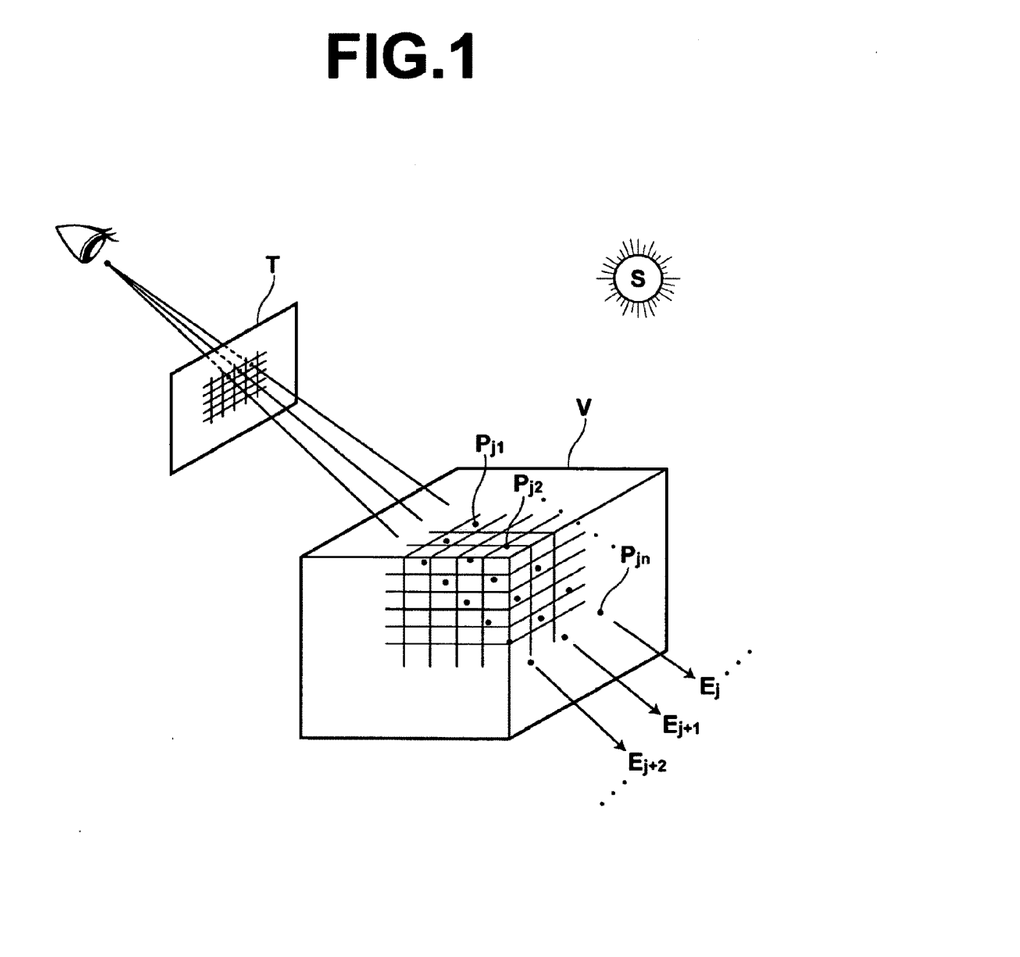
FIG. 1 is a drawing for explaining processing for generating a projection image by volume rendering method.

More specifically, as illustrated in FIG. 1, a plurality of search points $P_{ji}$ is set by sampling a three-dimensional image V at a predetermined interval along a plurality of visual lines $E_j$ (j=1, 2, - - -, L; L represents the number of visual lines). Then, a luminance value $b(P_{ji})$ and an opacity level $f(P_{ji})$ of each search point $P_{ji}$ are obtained in series along the visual line $E_j$, and an output pixel value of a pixel, projected on a projection plane, through which the visual line Ej passes is determined by Formula (3) below. Such processing is performed on each visual line to determine the output pixel values of all projection pixels on the projection plane, whereby a projection image is generated.

$$C_j = \sum_{i=1}^{n} \left( b(P_{ji}) \times f(P_{ji}) \prod_{k=1}^{i-1} (1 - f(P_{jk})) \right) \quad (3)$$

Here, the opacity level $f(P_{ji})$ of each search point $P_{ji}$ is determined according to the pixel value of the search point based on an opacity level predefined with respect to each pixel value. Therefore, by adjusting the setting of the opacity level allocated according to the pixel value, the visualization degree of the subject may be adjusted.

For example, as shown in FIGS. 2A to 4A, it is practiced to display, on a display screen, an image that changes from one side 1A to the other side 1B of two pseudo three-dimensional images generated under two different opacity level setting functions by providing sliding box 91 on the upper side of the display screen for displaying a projection image and sliding the position of slider 92 of slide box 91 from the left end ($\alpha$=0) to the right end ($\alpha$=1).

Figure 2A:
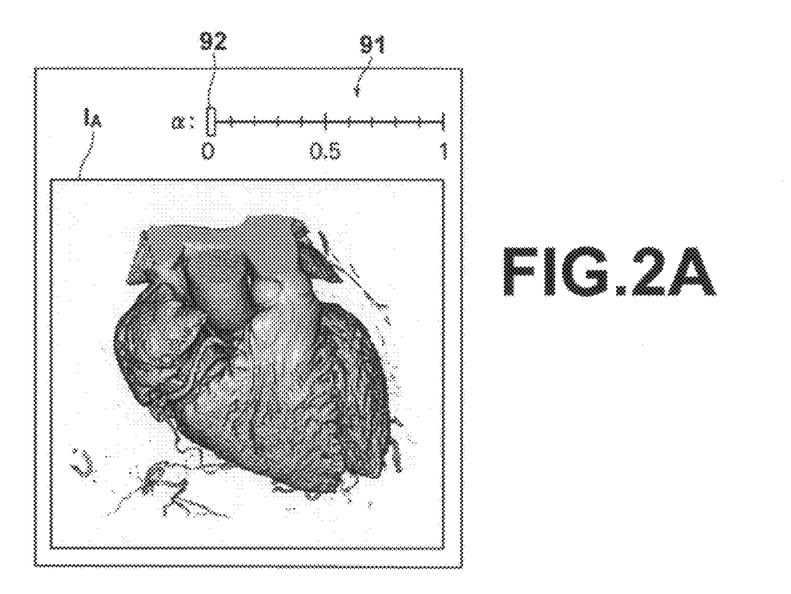
FIG. 2A shows a projection image generated in the start of changing phase (α=0).
Figure 2B:
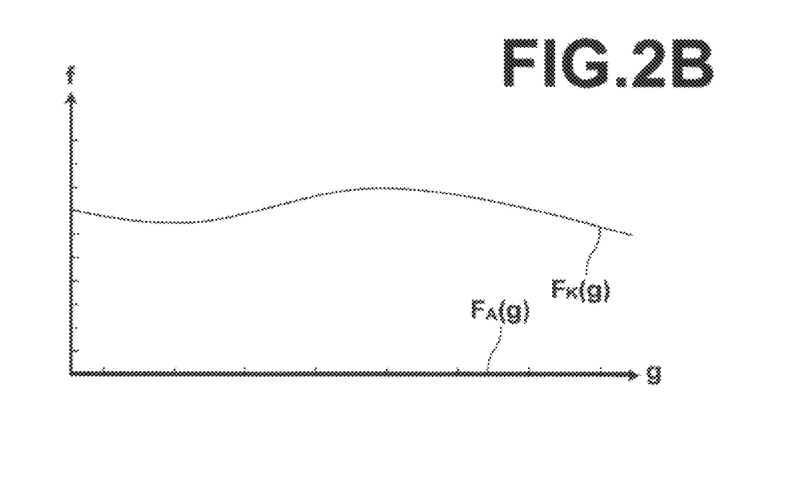
FIG. 2B is a graph illustrating opacity level setting functions applied to the generation of the projection image of FIG. 2A.
Figure 3A:
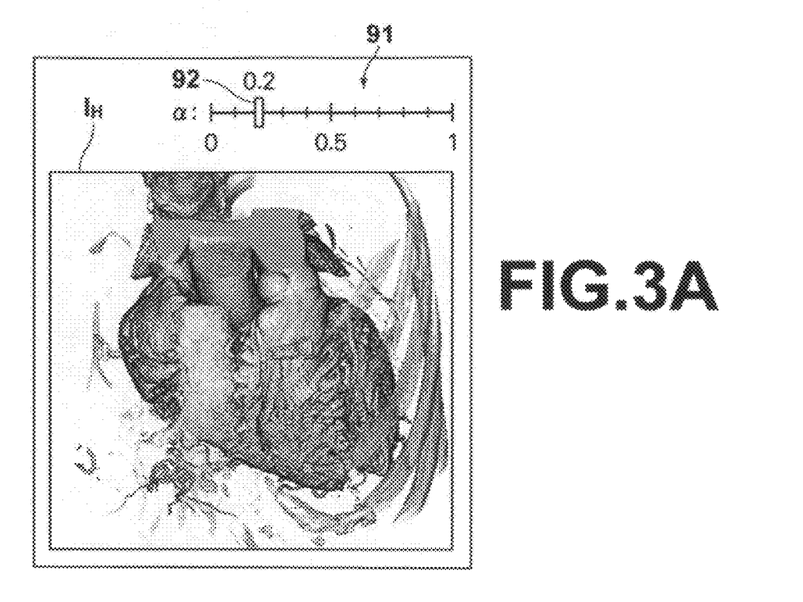
FIG. 3A shows an intermediate image generated by the conventional technology when the changing phase α is 0.2.
Figure 4A:
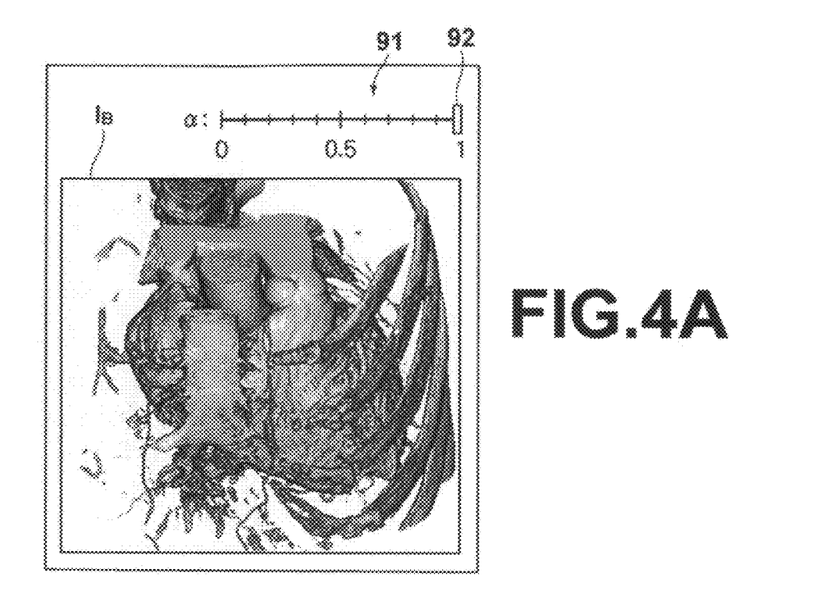
FIG. 4A shows a projection image generated at the end of changing phase (α=1).
Figure 4B:
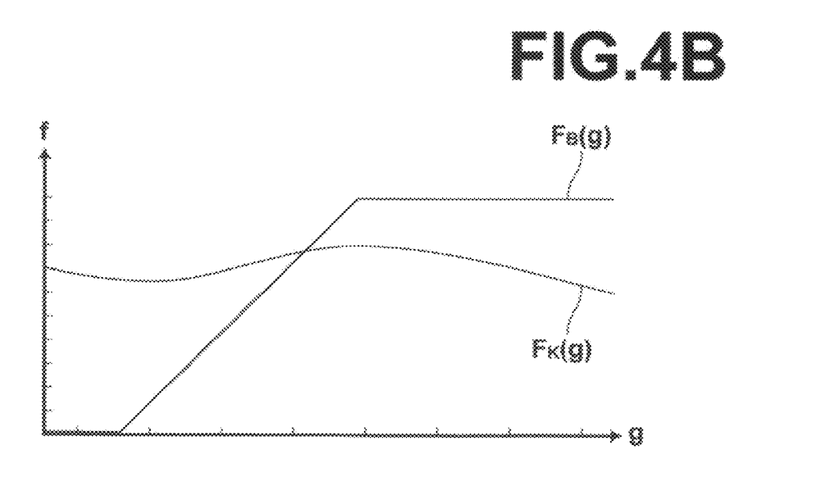
FIG. 4B is a graph illustrating opacity level setting functions applied to the generation of the projection image of FIG. 4A.

More specifically, when slider 92 is positioned at the left end ($\alpha$=0), a setting function $F_A(g)$ shown in the graph of FIG. 2B is applied and, as shown in FIG. 2A, an image $I_A$ with completely transparent ribs is generated, while when it is positioned at the right end ($\alpha$=1), a setting function $F_B(g)$ shown in the graph of FIG. 4B is applied and, as shown in FIG. 4A, an image $I_A$ with completely opaque ribs is generated. When slider 92 is positioned between the two ends (0<$\alpha$<1), a setting function $F_H$, obtained through linear interpolation of setting functions $F_A(g)$ and $F_B(g)$ by Formula (4) below according to the position $\alpha$ of slider 92, is applied and, as shown in FIG. 3A, an intermediate image $I_H$ in the middle of changing from image $I_A$ to image $I_B$ is generated as described, for example, in Japanese Unexamined Patent Publication No. 2005-202791.

$$F_H(g) = (1.0 - \alpha) F_A(g) + \alpha F_B(g) \quad (4)$$

Figure 3B:
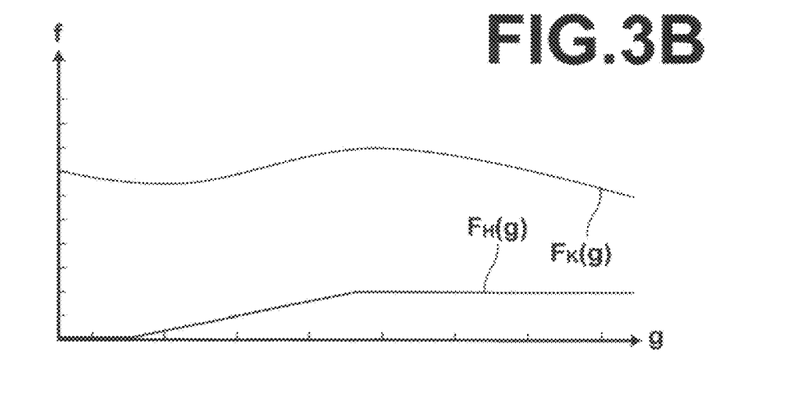
FIG. 3B is a graph illustrating opacity level setting functions applied to the generation of the projection image of FIG. 3A.

Note that the intermediate image shown in FIG. 3A is an image generated by applying the opacity level setting function $F_H(g)$ shown in the graph of FIG. 3B when slider 92 is positioned at $\alpha$=0.2. Here, each of the projection images $I_A$, $I_H$, $I_B$ is an image, by way of example, formed of a projection image of ribs superimposed with a projection image of a heart generated by ray casting a three-dimensional image of the heart under a setting function $F_K(g)$ of a given opacity level.

In the conventional technology described above, the opacity level allocated to each search point changes linearly according to Formula (4) above with respect to a linear change in the position $\alpha$ of slider 92, but when Formula (3) is substituted by the setting function $F_H(g)$ of Formula (4) above, Formula (3) becomes an (n+1)-th degree polynomial function and changes in the output pixel values of projection pixels are mostly nonlinear.

Figure 5:
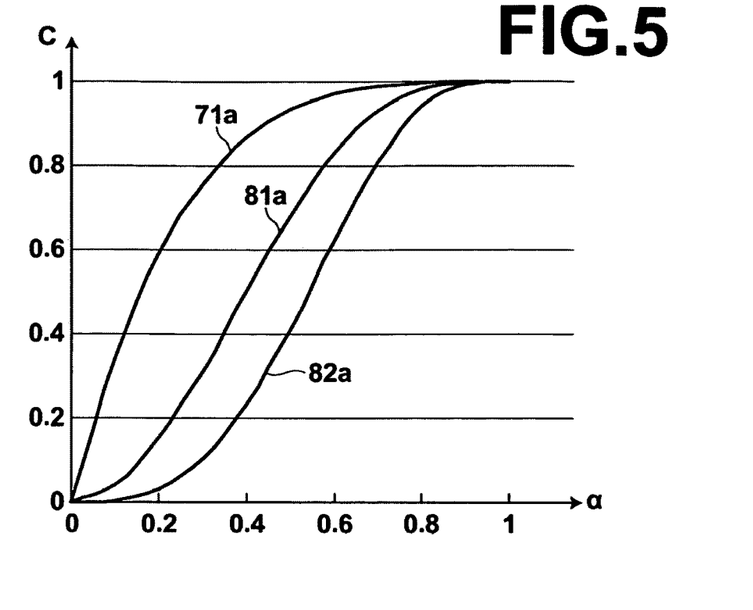
FIG. 5 is a graph illustrating changes in the output pixel value with respect to the changing phase.

For example, when generating a projection image that changes from a pseudo three-dimensional image $I_A$ generated under the condition of setting function $F_A(g)$=0.0 to a pseudo three-dimensional image $I_B$ generated under the condition of setting function $F_B(g)$=1.0 by volume rendering with the number of search points n=4 along the visual line $E_j$, the output pixel value C with respect to the changing phase $\alpha$ becomes like that shown in graph 71a of FIG. 5. In graph 71a, the output pixel value C changes sharply from the start of the change in $\alpha$($\alpha$=0), and when the changing phase $\alpha$ is 0.2, the output pixel value C has already passed more than half of the entire change and the change in the output pixel value C becomes extremely small as the changing phase approaches its end ($\alpha$=1).

Figure 6:
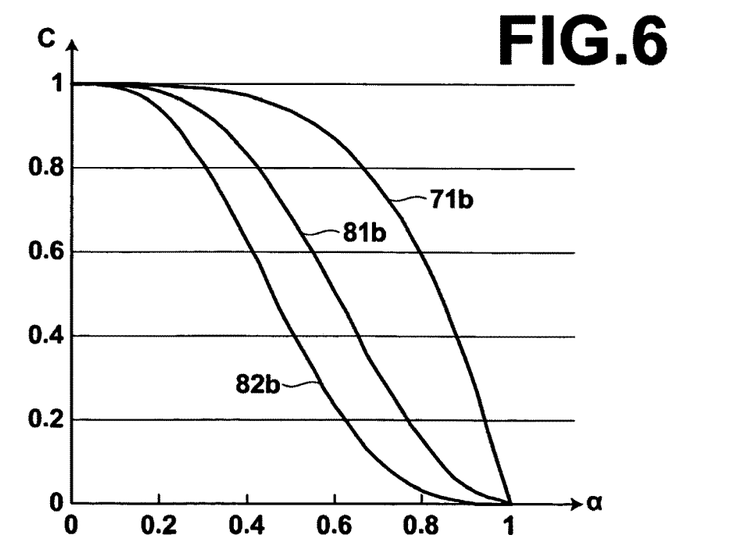
FIG. 6 is a graph illustrating changes in the output pixel value with respect to the changing phase.

Further, when generating a projection image that changes from a pseudo three-dimensional image $I_A$ generated under the condition of setting function $F_A(g)$=1.0 to a pseudo three-dimensional image $I_B$ generated under the condition of setting function $F_B(g)$=0.0, the output pixel value C with respect to the changing phase $\alpha$ becomes like that shown in graph 71b of FIG. 6.

In this way, the conventional technology described above has a problem that it can not obtain an intermediate image which changes linearly from one to the other of projection images only by linearly changing the changing phase $\alpha$.

In view of the circumstances described above, it is an object of the present invention to provide an intermediate image generation method, apparatus, and program capable of, when generating an intermediate image which is an image in the middle of changing from one to the other of two pseudo three-dimensional images generated by ray casting a three-dimensional image under two different setting conditions for an opacity level to be allocated according to a pixel value, generating an intermediate image that appears to change substantially linearly with a linear change in the changing phase.

SUMMARY OF THE INVENTION

An intermediate image generation method of the present invention is a method for generating an intermediate image which is an image in the middle of changing from one to the other of two pseudo three-dimensional images generated by ray casting a three-dimensional image from an arbitrary viewpoint under two different setting conditions for an opacity level to be allocated according to a pixel value, the method including the steps of:

determining an opacity level setting condition by determining an opacity level to be allocated according to each pixel value such that a variation in the opacity level for a change in a changing phase of the intermediate image become smaller as the changing phase approaches closer to a pseudo three-dimensional image generated under either one of the two different opacity level setting conditions in which a smaller value is allocated as the opacity level to be allocated according to each pixel value; and generating the intermediate image by ray casting the three-dimensional image from an arbitrary viewpoint under the determined opacity level setting condition.

The term "three-dimensional image" as used herein refers to a virtual three-dimensional image formed of three-dimensional image data constituted by multiple two dimensional images, and the term "pseudo three-dimensional image" as used herein refers to a two-dimensional image generated by volume rendering method and displayed in a three-dimensionally viewable manner.

An intermediate image generation apparatus of the present invention is an apparatus for generating an intermediate image which is an image in the middle of changing from one to the other of two pseudo three-dimensional images generated by ray casting a three-dimensional image from an arbitrary viewpoint under two different setting conditions for an opacity level to be allocated according to a pixel value, the apparatus including:

an opacity level determination means for determining an opacity level setting condition by determining an opacity level to be allocated according to each pixel value such that a variation in the opacity level for a change in a changing phase of the intermediate image become smaller as the changing phase approaches closer to a pseudo three-dimensional image generated under either one of the two different opacity level setting conditions in which a smaller value is allocated as the opacity level to be allocated according to each pixel value; and an intermediate image generation means for generating the intermediate image by ray casting the three-dimensional image from an arbitrary viewpoint under the opacity level setting condition determined by the opacity level determination means.

An intermediate image generation program of the present invention is a program for causing a computer to perform the intermediate image generation method described above.

In the method, apparatus, and program described above, the determination of the opacity level may be made by Formula (1) below.

$$F_\alpha(g) = (1.0 - t(\alpha)) \cdot F_A(g) + t(\alpha) \cdot F_B(g) \quad (1)$$

where, g is a pixel value, $F_A(g)$ is a function representing the opacity level setting condition applied to the generation of the pseudo three-dimensional image at the start of the changing phase, $F_B(g)$ is a function representing the opacity level setting condition applied to the generation of the pseudo three-dimensional image at the end of the changing phase, $\alpha$ ($0<\alpha<1$) represents the changing phase, $t(\alpha)$ is a monotonically increasing function, in which $t(\alpha)<u(\alpha)$ when $F_A(g) \leq F_B(g)$, while $t(\alpha)>u(\alpha)$ when $F_A(g)>F_B(g)$, $u(\alpha)=\alpha$, and $F_\alpha(g)$ is a function representing the opacity level setting condition applied to the generation of the intermediate image.

Further, the $t(\alpha)$ may be a function defined by Formula (2) below.

$$t(\alpha) = \begin{bmatrix} \alpha^x; & F_A(g) \leq F_B(g) \\ 1.0 - (1.0 - \alpha)^x; & F_A(g) > F_B(g) \end{bmatrix} \quad (2)$$

where, x is a real number in the range of $1<x\leq(-m/\log \beta)$, and m is the number of significant figures of a unit opacity level that causes an effective change in the opacity level, and $\beta$ is a unit variation in the changing phase that causes an effective change in the opacity level.

where, x is a real number in the range of $1<x\leq(-m/\log \beta)$, and m is the number of significant figures of a unit opacity level that causes an effective change in the opacity level, and $\beta$ is a unit variation in the changing phase that causes an effective change in the opacity level.

According to the intermediate image generation method, apparatus, and program, when generating an intermediate image which is an image in the middle of changing from one to the other of two pseudo three-dimensional images generated by ray casting a three-dimensional image under two different opacity level setting conditions, an opacity level to be allocated according to each pixel value is determined using a nonlinear function in which a variation in the opacity level for a change in a changing phase of the intermediate image become smaller as the changing phase approaches closer to a pseudo three-dimensional image generated under either one of the two different opacity level setting conditions in which a smaller value is allocated as the opacity level to be allocated according to each pixel value, and an intermediate image is generated by ray casting the three-dimensional image from an arbitrary viewpoint under the determined opacity level setting condition. This allows an intermediate image that appears to change substantially linearly with a linear change in the changing phase to be generated.

In the method, apparatus, and program described above, the determination of the opacity level may be made by Formula (1) below.

$$F_\alpha(g) = (1.0 - t(\alpha)) \cdot F_A(g) + t(\alpha) \cdot F_B(g) \quad (1)$$

where, g is a pixel value, $F_A(g)$ is a function representing the opacity level setting condition applied to the generation of the pseudo three-dimensional image at the start of the changing phase, $F_B(g)$ is a function representing the opacity level setting condition applied to the generation of the pseudo three-dimensional image at the end of the changing phase, $\alpha$ ($0<\alpha<1$) represents the changing phase, $t(\alpha)$ is a monotonically increasing function, in which $t(\alpha)<u(\alpha)$ when $F_A(g) \leq F_B(g)$, while $t(\alpha)>u(\alpha)$ when $F_A(g) \leq F_B(g)$, $u(\alpha)=\alpha$, and $F_\alpha(g)$ is a function representing the opacity level setting condition applied to the generation of the intermediate image.

For example, when generating a projection image that changes from a pseudo three-dimensional image $I_A$ generated under the condition of setting function $F_A(g)=0.0$ to a pseudo three-dimensional image $I_B$ generated under the condition of setting function $F_B(g)=1.0$ by volume rendering with four search points set along a visual line, if the opacity level determination is made by Formula (1) above using the function $t(\alpha)$ defined by Formula (2) below, graphs 81a (x=2) and 82a (x=3) of the output pixel value C with respect to the changing phase α become closer to linear in comparison with graph 71a of the conventional technology, as shown in FIG. 5. Further, when generating a projection image that changes from a pseudo three-dimensional image $I_A$ generated under the condition of setting function $F_A(g)=1.0$ to a pseudo three-dimensional image $I_B$ generated under the condition of setting function $F_B(g)=0.0$, if the opacity level determination is made by Formula (1) above using the function $t(\alpha)$ defined by Formula (2) below, graphs 81b (x=2) and 82b (x=3) of the output pixel value C with respect to the changing phase α become closer to linear in comparison with graph 71b of the conventional technology, as shown in FIG. 6. This allows an intermediate image which appears to change substantially linearly with a linear change in the changing phase to be generated.

$$t(\alpha) = \begin{bmatrix} \alpha^x; & F_A(g) \leq F_B(g) \\ 1.0 - (1.0 - \alpha)^x; & F_A(g) > F_B(g) \end{bmatrix} \quad (2)$$

where, x is a real number in the range of $1 < x \leq (-m/\log \beta)$, and m is the number of significant figures of a unit opacity level that causes an effective change in the opacity level, and β is a unit variation in the changing phase that causes an effective change in the opacity level.

DESCRIPTION OF THE INVENTION

Hereinafter, an embodiment of the present invention will be described with reference to the accompanying drawings.

Figure 7:
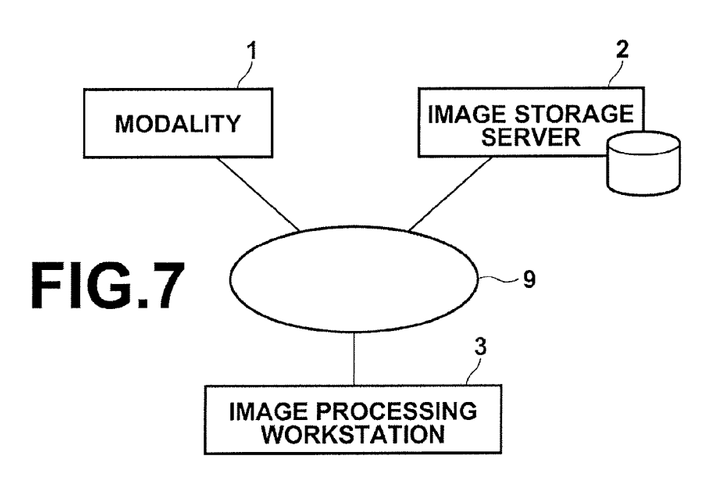
FIG. 7 is a schematic configuration diagram of a three-dimensional medical image processing system according to an embodiment of the present invention.

FIG. 7 is a hardware configuration diagram of a three-dimensional medical image processing system according to an embodiment of the present invention, illustrating an overview thereof. As shown in FIG. 7, the system includes modality 1, image storage server 2, and image processing workstation 3 communicatably linked to each other via network 9.

Modality 1 is a system for obtaining a three-dimension medical image V (three-dimensional image) representing a test body and more specifically, it is a CT system, an MRI system, an ultrasonic diagnostic system, or the like.

Image storage server 2 is a computer for storing in a database and managing the three-dimensional medical image V obtained by modality 1 and a medical image generated through image processing performed in image processing workstation 3, and includes a large capacity external memory unit and database management software (e.g., object relational database (ORDB) management software).

Image processing workstation 3 is a computer for performing, in response to a request from a radiologist, image processing on a three-dimensional medical image V obtained from modality 1 or image storage server 2 and displaying a generated image. It includes, in particular, an input device, such as a keyboard, a mouse, or the like, for receiving a request from a radiologist, a main storage unit with a capacity sufficient of storing an obtained three-dimensional medical image V, and a display for displaying a generated image.

The storage format of image data and communication between each component of the system via network 9 are based on DICOM (Digital Imaging and Communication in Medicine) protocol or the like.

Figure 8:
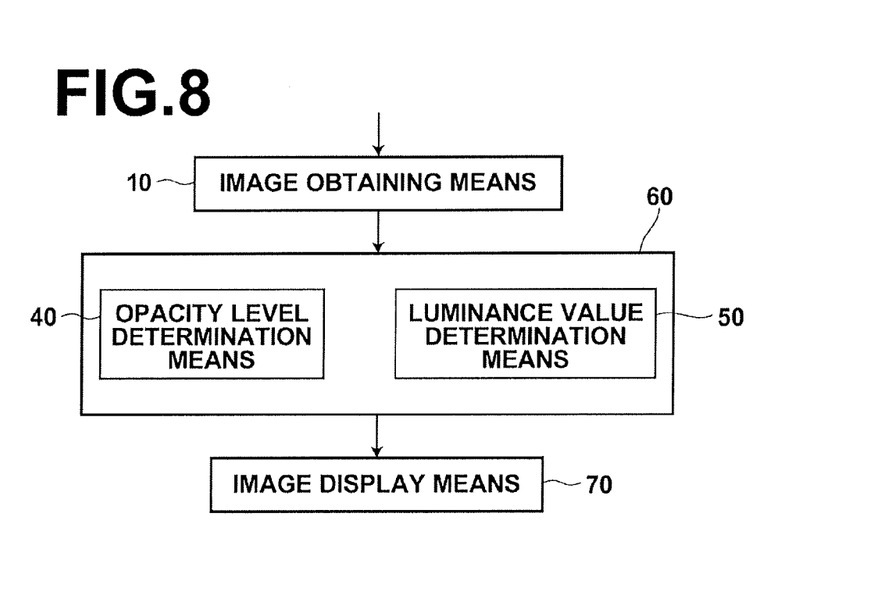
FIG. 8 is a block diagram of a volume rendering function of the image processing workstation shown in FIG. 7.

FIG. 8 is a block diagram, illustrating a portion of image processing workstation 3 related to the volume rendering function. As shown in the drawing, image processing workstation 3 includes image obtaining means 10 for obtaining a three-dimensional medical image V of a target patient for radiology reading from modality 1 or image storage server 2 in response to a request from a radiologist, ray casting means 60 for determining pixel values of pixels on a projection plane using luminance values and opacity levels of a plurality of search points obtained by sampling a three-dimensional medical image V at a predetermined interval along a plurality of visual lines, each connection an arbitrary viewpoint and each pixel on the projection plane, and generating a volume rendering image (pseudo three-dimensional image), and image display means 70 for displaying the generated volume rendering image on a display. Ray casting means 60 includes opacity level determination means 40 and luminance value determination means 50 for determining a luminance value and an opacity level at each search point respectively.

Next, processing flow of the medical image processing system, in particular, of image processing workstation 3, for generating a volume rendering image will be described.

First, image obtaining means 10 obtains a three-dimensional medical image V of a target patient of radiology reading from modality 1 or image storage server in response to a request from a radiologist. The three-dimensional medical image V is generated by dividing a multi-slice image into pixels (voxels) and arranging the pixels in a three-dimensional coordinate space, in which the position of each pixel is defined by a three-dimensional coordinate system with left-right directions of a subject as x-axis, front-back directions as y-axis, and up-down directions as z-axis, and the pixel value of each voxel is related to the coordinates of the position of the voxel.

Then, ray casting means 60 obtains pixel values (output pixel values) of pixels forming a volume rendering image of the three-dimensional medical image V obtained by image obtaining means 10. First, based on a viewpoint, light source S, and a projection plane F (size, position, and number of pixels) set from an initial setting file or by input from a radiologist through a mouse or a keyboard, for example, a plurality of search points $P_{ji}$(i=1, 2, - - - , n; n represents the number of search points on visual line $E_j$) is set by sampling the three-dimensional medical image V at a predetermined interval along a plurality of visual lines $E_j$(j=1, 2, - - - , L; L represents the number of visual lines), each connecting the viewpoint and each pixel on the projection plane F. Then, an opacity level $f(P_{ji})$ and a luminance value $b(P_{ji})$ at each search point $P_{ji}$ are obtained in series along a visual line $E_j$ by opacity level determination means 40 and luminance value determination means 50, to be described later, respectively. Then, the products of these values are added up, as shown in Formula (3) below, and when a cumulative value of opacity levels f reaches a predetermined threshold value or when the ray gets out of the target three-dimensional medical image V, the processing with respect to the visual line $E_j$ is completed and the added-up result is determined as the output pixel value $C_j$ of the projection pixel on the projection plane through which the visual line $E_j$ passes.

$$C_j = \sum_{i=1}^{n} \left( b(P_{ji}) \times f(P_{ji}) \prod_{k=1}^{i-1} (1 - f(P_{jk})) \right) \quad (3)$$

Such processing is performed on each visual line to determine the output pixel values of all projection pixels on the projection plane, whereby a volume rendering image is generated. The volume rendering image generated in the manner as described above is displayed on the display of workstation 3 by image display means 70.

Processing of opacity level determination means 40 for determining the opacity level $f(P_{ji})$ at each search point $P_{ji}$ will now be described.

If a setting condition F(g) for allocating the opacity level according to the pixel value is given in advance, the opacity level $f(P_{ji})$ at a search point $P_{ji}$ is determined according to the pixel value $g(P_{ji})$ at the search point $P_{ji}$ based on the setting condition F(g). Note that the pixel value $g(P_{ji})$ at a search point $P_{ji}$ is calculated through linear interpolation of eight voxels forming a grid surrounding the search point $P_{ji}$. The same applies hereinafter.

In the mean time, when generating an intermediate image $I_\alpha$ which is an image in the middle of changing from a pseudo three-dimensional image $I_A$ generated by ray casting a three-dimensional image under a setting function $F_A(g)$ that allocates the opacity level according to the pixel value to a pseudo three-dimensional image $I_B$ generated by ray casting the three-dimensional image under a setting function $F_B(g)$, the opacity level $f(P_{ji})$ of a search point $P_{ji}$ is determined according to the pixel value $g(P_{ji})$ of the search point $P_{ji}$ based on a setting function $F_\alpha(g)$ obtained by interpolating the setting functions $F_A(g)$ and $F_B(g)$.

More specifically, the setting function $F_\alpha(g)$ is determined by determining an opacity level f to be allocated according to each pixel value g such that a variation in the opacity level to be allocated for a change in a changing phase α becomes smaller as the changing phase α(0<α<1) approaches closer to a pseudo three-dimensional image generated under either one of two different opacity level setting functions $F_A(g)$ and $F_B(g)$ in which a smaller value is allocated as the opacity level to be allocated according to each pixel value g. Then, based on the determined opacity level setting function $F_\alpha(g)$, the opacity level $f(P_{ji})$ of a search point $P_{ji}$ is determined according to the pixel value $g(P_{ji})$ of the search point $P_{ji}$ using Formula (5) below.

$$f(P_{ji}) = F_\alpha(g) \text{ where } g = g(P_{ji}) \quad (5)$$

As for the opacity level setting condition $F_\alpha(g)$, for example, the condition calculated by Formula (1) below may be used.

$$F_\alpha(g) = (1.0 - t(\alpha)) \cdot F_A(g) + t(\alpha) \cdot F_B(g) \quad (1)$$

where, t(α) is an interpolation coefficient function and, for example, the function defined by Formula (2) below may be used.

$$t(\alpha) = \begin{cases} \alpha^x; & F_A(g) \le F_B(g) \\ 1.0 - (1.0 - \alpha)^x; & F_A(g) > F_B(g) \end{cases} \quad (2)$$

where, x is a real number in the range of 1<x≦(−m/log β), and m is the number of significant figures of a unit opacity level that causes an effective change in the opacity level, and β is a unit variation in the changing phase that causes an effective change in the opacity level.

Next, processing of luminance value determination means 50 for determining the luminance value b $(P_{ji})$ at each search point $P_{ji}$, will be described. The luminance value b $(P_{ji})$ at each search point $P_{ji}$ is calculated by Formula (6) below.

$$b(P_{ji}) = h(N(P_{ji}) \cdot L) \times c(P_{ji}) \quad (6)$$

where, h is a shading coefficient due to diffuse reflection. In the present embodiment, environmental light and specular reflection light are disregarded. $N(P_{ji})$ is a normal vector at a search point $P_{ji}$ which is given by Formula (7) below.

$$N(P_{ji}) = \frac{\nabla f(P_{ji})}{|\nabla f(P_{ji})|} \quad (7)$$

where, $\nabla f(P_{ji})$ is a gradient of opacity level at a search point $P_{ji}$, and is calculated by Formula (8) below using opacity levels f of six adjacent points adjacent in x-axis, y-axis, or z-axis direction. Here, $P_{ji}$=(x, y, z) for the purpose of simplification.

$$\nabla f(P_{ji}) = \nabla f \begin{pmatrix} x \\ y \\ z \end{pmatrix} = \begin{pmatrix} \frac{f(x+\Delta x, y, z) - f(x-\Delta x, y, z)}{2} \\ \frac{f(x, y+\Delta y, z) - f(x, y-\Delta y, z)}{2} \\ \frac{f(x, y, z+\Delta z) - f(x, y, z-\Delta z)}{2} \end{pmatrix} \quad (8)$$

Further, L represents a unit tangent vector from the search point to the light source S, "·" is an inner product of the vector, and $c(P_{ji})$ is color information allocated based on color information defined in advance with respect to each tissue (with respect to each pixel value, such as a CT value) of the test body.

The opacity level determination and luminance value determination are independent processing, and therefore, either of them may be performed first when they are performed in series, or they may be performed in parallel simultaneously.

In this way, in the three-dimensional medical image processing system according to an embodiment of the present invention, when generating an intermediate image which is an image in the middle of changing from one to the other of two pseudo three-dimensional images generated by ray casting a three-dimensional image from an arbitrary viewpoint under two different setting conditions for an opacity level to be allocated according to a pixel value, opacity level determination means 40 determines the opacity level setting condition such that a variation in the opacity level to be allocated for a change in the changing phase becomes smaller as the changing phase approaches closer to a pseudo three-dimensional image generated under either one of two different opacity level setting conditions in which a smaller value is allocated as the opacity level to be allocated according to each pixel value, and ray casting means 60 generates the intermediate image by ray casting the three-dimensional image from an arbitrary viewpoint under the determined opacity level setting condition. This allows an intermediate image which appears to change substantially linearly with a linear change in the changing phase to be generated.

It will be appreciated that various changes and modifications made in the system configuration, process flow, module configuration, and the like in the embodiment described above without departing from the spirit of the present invention are included in the technical scope of the present invention. The embodiment described above is provided by way of example and any part of the description should not be construed as limiting the technical scope of the invention.

For example, in the embodiment described above, both image processing and image display are carried out in image processing workstation 3, but the image processing may be performed by a separate image processing server additionally provided and connected to network 9. This allows distributed processing which, for example, may eliminate the need to provide a plurality of high performance image processing workstations where an image is displayed on a plurality of terminals, whereby the overall system cost is reduced.

The invention claimed is:

1. An intermediate image generation method for generating an intermediate image which is an image in the middle of changing from one to the other of two pseudo three-dimensional images generated by ray casting a three-dimensional image from an arbitrary viewpoint under two different setting conditions for an opacity level to be allocated according to a pixel value, the method comprising the steps of:
   determining an opacity level setting condition by determining an opacity level to be allocated according to each pixel value such that a variation in the opacity level for a change in a changing phase of the intermediate image becomes smaller as the changing phase approaches closer to a pseudo three-dimensional image generated under either one of the two different opacity level setting conditions in which a smaller value is allocated as the opacity level to be allocated according to each pixel value; and
   generating the intermediate image by ray casting the three-dimensional image from an arbitrary viewpoint under the determined opacity level setting condition, such that the intermediate image appears to change substantially linearly with a linear change in the changing phase,
   wherein the determination of the opacity level is made by following Formula (1):

$$F_\alpha(g) = (1.0 - t(\alpha)) \cdot F_A(g) + t(\alpha) \cdot F_B(g) \quad (1)$$

where g is a pixel value;
$F_A(g)$ is a function representing the opacity level setting condition applied to the generation of the pseudo three-dimensional image at the start of the changing phase;
$F_B(g)$ is a function representing the opacity level setting condition applied to the generation of the pseudo three-dimensional image at the end of the changing phase;
$\alpha(0<\alpha<1)$ represents the changing phase;
$t(\alpha)$ is a monotonically increasing function, in which $t(\alpha)<u(\alpha)$ when $F_A(g) \leq F_B(g)$, while $t(\alpha)>u(\alpha)$ when $F_A(g)>F_B(g)$, $u(\alpha)=\alpha$; and
$F_\alpha(g)$ is a function representing the opacity level setting condition applied to the generation of the intermediate image.

2. An intermediate image generation method for generating an intermediate image which is an image in the middle of changing from one to the other of two pseudo three-dimensional images generated by ray casting a three-dimensional image from an arbitrary viewpoint under two different setting conditions for an opacity level to be allocated according to a pixel value, the method comprising the steps of:
   determining an opacity level setting condition by determining an opacity level to be allocated according to each pixel value such that a variation in the opacity level for a change in a changing phase of the intermediate image becomes smaller as the changing phase approaches closer to a pseudo three-dimensional image generated under either one of the two different opacity level setting conditions in which a smaller value is allocated as the opacity level to be allocated according to each pixel value; and
   generating the intermediate image by ray casting the three-dimensional image from an arbitrary viewpoint under the determined opacity level setting condition, such that the intermediate image appears to change substantially linearly with a linear change in the changing phase,
   wherein the determination of the opacity level is made by following Formula (1):

$$F_\alpha(g) = (1.0 - t(\alpha)) \cdot F_A(g) + t(\alpha) \cdot F_B(g) \quad (1)$$

where g is a pixel value;
$F_A(g)$ is a function representing the opacity level setting condition applied to the generation of the pseudo three-dimensional image at the start of the changing phase;
$F_B(g)$ is a function representing the opacity level setting condition applied to the generation of the pseudo three-dimensional image at the end of the changing phase;
$\alpha(0<\alpha<1)$ represents the changing phase;
$t(\alpha)$ is a monotonically increasing function, in which $t(\alpha)<u(\alpha)$ when $F_A(g) \leq F_B(g)$, while $t(\alpha)>u(\alpha)$ when $F_A(g)>F_B(g)$, $u(\alpha)=\alpha$; and
$F_\alpha(g)$ is a function representing the opacity level setting condition applied to the generation of the intermediate image; and
wherein the $t(\alpha)$ is a function defined by following Formula (2):

$$t(\alpha) = \begin{bmatrix} \alpha^x; & F_A(g) \leq F_B(g) \\ 1.0 - (1.0 - \alpha)^x; & F_A(g) > F_B(g) \end{bmatrix} \quad (2)$$

where x is a real number in the range of $1<x\leq(-m/\log \beta)$;
m is the number of significant figures of a unit opacity level that causes an effective change in the opacity level; and
$\beta$ is a unit variation in the changing phase that causes an effective change in the opacity level.

3. An intermediate image generation apparatus for generating an intermediate image which is an image in the middle of changing from one to the other of two pseudo three-dimensional images generated by ray casting a three-dimensional image from an arbitrary viewpoint under two different setting conditions for an opacity level to be allocated according to a pixel value, the apparatus comprising:

an opacity level determination means for determining an opacity level setting condition by determining an opacity level to be allocated according to each pixel value such that a variation in the opacity level for a change in a changing phase of the intermediate image becomes smaller as the changing phase approaches closer to a pseudo three-dimensional image generated under either one of the two different opacity level setting conditions in which a smaller value is allocated as the opacity level to be allocated according to each pixel value; and an intermediate image generation means for generating the intermediate image by ray casting the three-dimensional image from an arbitrary viewpoint under the opacity level setting condition determined by the opacity level determination means, such that the intermediate image appears to change substantially linearly with a linear change in the changing phase, wherein the opacity level determination means makes the determination of the opacity level by following Formula (1):

$$F_\alpha(g) = (1.0 - t(\alpha)) \cdot F_A(g) + t(\alpha) \cdot F_B(g) \quad (1)$$

where g is a pixel value;
$F_A(g)$ is a function representing the opacity level setting condition applied to the generation of the pseudo three-dimensional image at the start of the changing phase;
$F_B(g)$ is a function representing the opacity level setting condition applied to the generation of the pseudo three-dimensional image at the end of the changing phase;
$\alpha (0 < \alpha < 1)$ represents the changing phase;
$t(\alpha)$ is a monotonically increasing function, in which $t(\alpha) < u(\alpha)$ when $F_A(g) \leq F_B(g)$, while $t(\alpha) > u(\alpha)$ when $F_A(g) > F_B(g)$, $u(\alpha) = \alpha$; and
$F_\alpha(g)$ is a function representing the opacity level setting condition applied to the generation of the intermediate image.

4. An intermediate image generation apparatus for generating an intermediate image which is an image in the middle of changing from one to the other of two pseudo three-dimensional images generated by ray casting a three-dimensional image from an arbitrary viewpoint under two different setting conditions for an opacity level to be allocated according to a pixel value, the apparatus comprising:

an opacity level determination means for determining an opacity level setting condition by determining an opacity level to be allocated according to each pixel value such that a variation in the opacity level for a change in a changing phase of the intermediate image becomes smaller as the changing phase approaches closer to a pseudo three-dimensional image generated under either one of the two different opacity level setting conditions in which a smaller value is allocated as the opacity level to be allocated according to each pixel value; and an intermediate image generation means for generating the intermediate image by ray casting the three-dimensional image from an arbitrary viewpoint under the opacity level setting condition determined by the opacity level determination means. such that the intermediate image appears to change substantially linearly with a linear change in the changing phase, wherein the opacity level determination means makes the determination of the opacity level by following Formula (1):

$$F_\alpha(g) = (1.0 - t(\alpha)) \cdot F_A(g) + t(\alpha) \cdot F_B(g) \quad (1)$$

where g is a pixel value;
$F_A(g)$ is a function representing the opacity level setting condition applied to the generation of the pseudo three-dimensional image at the start of the changing phase:
$F_B(g)$ is a function representing the opacity level setting condition applied to the generation of the pseudo three-dimensional image at the end of the changing phase;
$\alpha (0 < \alpha < 1)$ represents the changing phase;
$t(\alpha)$ is a monotonically increasing function, in which $t(\alpha) < u(\alpha)$ when $F_A(g) \leq F_B(g)$, while $t(\alpha) > u(\alpha)$ when $F_A(g) > F_B(g)$, $u(\alpha) = \alpha$; and
$F_\alpha(g)$ is a function representing the opacity level setting condition applied to the generation of the intermediate image, and wherein the $t(\alpha)$ is a function defined by following Formula (2):

$$t(\alpha) = \begin{bmatrix} \alpha^x; & F_A(g) \leq F_B(g) \\ 1.0 - (1.0 - \alpha)^x; & F_A(g) > F_B(g) \end{bmatrix} \quad (2)$$

where x is a real number in the range of $1 < x \leq (-m/\log \beta)$;
m is the number of significant figures of a unit opacity level that causes an effective change in the opacity level; and
$\beta$ is a unit variation in the changing phase that causes an effective change in the opacity level.

5. An intermediate image generation method for generating an intermediate image which is an image in the middle of changing from one to the other of two pseudo three-dimensional images generated by ray casting a three-dimensional image from an arbitrary viewpoint under two different setting conditions for an opacity level to be allocated according to a pixel value, the method comprising the steps of:

determining an opacity level setting condition by determining an opacity level to be allocated according to each pixel value such that a variation in the opacity level for a change in a changing phase of the intermediate image becomes smaller as the changing phase approaches closer to a pseudo three-dimensional image generated under either one of the two different opacity level setting conditions in which a smaller value is allocated as the opacity level to be allocated according to each pixel value; and generating the intermediate image by ray casting the three-dimensional image from an arbitrary viewpoint under the determined opacity level setting condition, wherein the determination of the opacity level is made by following Formula (1):

$$F_\alpha(g) = (1.0 - t(\alpha)) \cdot F_A(g) + t(\alpha) \cdot F_B(g) \quad (1)$$

where g is a pixel value;
$F_A(g)$ is a function representing the opacity level setting condition applied to the generation of the pseudo three-dimensional image at the start of the changing phase;
$F_B(g)$ is a function representing the opacity level setting condition applied to the generation of the pseudo three-dimensional image at the end of the changing phase;
$\alpha (0 < \alpha < 1)$ represents the changing phase;
$t(\alpha)$ is a monotonically increasing function, in which $t(\alpha) < u(\alpha)$ when $F_A(g) \leq F_B(g)$, while $t(\alpha) > u(\alpha)$ when $F_A(g) > F_B(g)$, $u(\alpha) = \alpha$; and
$F_\alpha(g)$ is a function representing the opacity level setting condition applied to the generation of the intermediate image.

6. The intermediate image generation method of claim 5, wherein the t(α) is a function defined by following Formula (2):

$$t(\alpha) = \begin{bmatrix} \alpha^x; & F_A(g) \leq F_B(g) \\ 1.0 - (1.0 - \alpha)^x; & F_A(g) > F_B(g) \end{bmatrix} \quad (2)$$

where x is a real number in the range of $1 < x \leq (-m/\log \beta)$;
m is the number of significant figures of a unit opacity level that causes an effective change in the opacity level; and
β is a unit variation in the changing phase that causes an effective change in the opacity level.

7. An intermediate image generation apparatus for generating an intermediate image which is an image in the middle of changing from one to the other of two pseudo three-dimensional images generated by ray casting a three-dimensional image from an arbitrary viewpoint under two different setting conditions for an opacity level to be allocated according to a pixel value, the apparatus comprising:
an opacity level determination means for determining an opacity level setting condition by determining an opacity level to be allocated according to each pixel value such that a variation in the opacity level for a change in a changing phase of the intermediate image becomes smaller as the changing phase approaches closer to a pseudo three-dimensional image generated under either one of the two different opacity level setting conditions in which a smaller value is allocated as the opacity level to be allocated according to each pixel value; and
an intermediate image generation means for generating the intermediate image by ray casting the three-dimensional image from an arbitrary viewpoint under the opacity level setting condition determined by the opacity level determination means,
wherein the opacity level determination means makes the determination of the opacity level by following Formula (1):

$$F_\alpha(g) = (1.0 - t(\alpha)) \cdot F_A(g) + t(\alpha) \cdot F_B(g) \quad (1)$$

where g is a pixel value;
$F_A(g)$ is a function representing the opacity level setting condition applied to the generation of the pseudo three-dimensional image at the start of the changing phase;
$F_B(g)$ is a function representing the opacity level setting condition applied to the generation of the pseudo three-dimensional image at the end of the changing phase;
α(0<α<1) represents the changing phase;
t(α) is a monotonically increasing function, in which t(α)<u(α) when $F_A(g) \leq F_B(g)$, while t(α)>u(α) when $F_A(g) > F_B(g)$, u(α)=α; and
$F_\alpha(g)$ is a function representing the opacity level setting condition applied to the generation of the intermediate image.

8. The intermediate image generation apparatus of claim 7, wherein the t(α) is a function defined by following Formula (2):

$$t(\alpha) = \begin{bmatrix} \alpha^x; & F_A(g) \leq F_B(g) \\ 1.0 - (1.0 - \alpha)^x; & F_A(g) > F_B(g) \end{bmatrix} \quad (2)$$

where x is a real number in the range of $1 < x \leq (-m/\log \beta)$;
m is the number of significant figures of a unit opacity level that causes an effective change in the opacity level; and
β is a unit variation in the changing phase that causes an effective change in the opacity level.

9. A non-transitory computer readable recording medium on which is recorded an intermediate image generation program for generating an intermediate image which is an image in the middle of changing from one to the other of two pseudo three-dimensional images generated by ray casting a three-dimensional image from an arbitrary viewpoint under two different setting conditions for an opacity level to be allocated according to a pixel value, the program causing a computer to perform the steps of:
determining an opacity level setting condition by determining an opacity level to be allocated according to each pixel value such that a variation in the opacity level for a change in a changing phase of the intermediate image becomes smaller as the changing phase approaches closer to a pseudo three-dimensional image generated under either one of the two different opacity level setting conditions in which a smaller value is allocated as the opacity level to be allocated according to each pixel value; and
generating the intermediate image by ray casting the three-dimensional image from an arbitrary viewpoint under the determined opacity level setting condition,
wherein the determination of the opacity level is made by following Formula (1):

$$F_\alpha(g) = (1.0 - t(\alpha)) \cdot F_A(g) + t(\alpha) \cdot F_B(g) \quad (1)$$

where g is a pixel value;
$F_A(g)$ is a function representing the opacity level setting condition applied to the generation of the pseudo three-dimensional image at the start of the changing phase;
$F_B(g)$ is a function representing the opacity level setting condition applied to the generation of the pseudo three-dimensional image at the end of the changing phase;
α(0<α<1) represents the changing phase;
t(α) is a monotonically increasing function, in which t(α)<u(α) when $F_A(g) \leq F_B(g)$, while t(α)>u(α) when $F_A(g) > F_B(g)$, u(α)=α; and
$F_\alpha(g)$ is a function representing the opacity level setting condition applied to the generation of the intermediate image.

* * * * *